(12) United States Patent
Gazit et al.

(10) Patent No.: US 9,218,661 B2
(45) Date of Patent: Dec. 22, 2015

(54) IMAGE ANALYSIS FOR SPECIFIC OBJECTS

(75) Inventors: Tiferet T. Gazit, Ra'anana (IL); Yosef Y. Markov, Ra'anana (IL); Uri U. Einav, Yuvalim (IL); Hadas H. Padan, Ra'anana (IL); Guy E. Engelhard, Kiryat Ono (IL)

(73) Assignee: Algotec Systems Ltd., Ra'anana (IL)

( * ) Notice: Subject to any disclaimer, the term of this patent is extended or adjusted under 35 U.S.C. 154(b) by 165 days.

(21) Appl. No.: 14/005,652

(22) PCT Filed: Apr. 5, 2012

(86) PCT No.: PCT/US2012/032341
§ 371 (c)(1),
(2), (4) Date: Sep. 17, 2013

(87) PCT Pub. No.: WO2012/138871
PCT Pub. Date: Oct. 11, 2012

(65) Prior Publication Data
US 2014/0016845 A1    Jan. 16, 2014

Related U.S. Application Data

(60) Provisional application No. 61/473,250, filed on Apr. 8, 2011.

(51) Int. Cl.
| | |
|---|---|
| G06T 7/00 | (2006.01) |
| A61B 5/055 | (2006.01) |
| G06T 7/20 | (2006.01) |
| A61B 6/00 | (2006.01) |
| A61B 5/00 | (2006.01) |

(52) U.S. Cl.
CPC .............. *G06T 7/0016* (2013.01); *A61B 5/055* (2013.01); *G06T 7/0038* (2013.01); *G06T 7/20* (2013.01); *G06T 7/2006* (2013.01); *A61B 5/004* (2013.01); *A61B 5/0013* (2013.01); *A61B 5/0035* (2013.01); *A61B 6/469* (2013.01); *A61B 6/5217* (2013.01); *A61B 6/5235* (2013.01); *A61B 2576/00* (2013.01); *G06T 2207/10076* (2013.01); *G06T 2207/10081* (2013.01); *G06T 2207/10088* (2013.01); *G06T 2207/10104* (2013.01); *G06T 2207/20036* (2013.01); *G06T 2207/20101* (2013.01); *G06T 2207/20104* (2013.01); *G06T 2207/20148* (2013.01); *G06T 2207/30056* (2013.01); *G06T 2207/30061* (2013.01); *G06T 2207/30096* (2013.01)

(58) Field of Classification Search
None
See application file for complete search history.

(56) References Cited

U.S. PATENT DOCUMENTS

| | | | |
|---|---|---|---|
| 6,373,998 B2 | 4/2002 | Thirion et al. | |
| 7,773,791 B2 | 8/2010 | Simon et al. | |
| 7,844,087 B2 | 11/2010 | Ray et al. | |
| 8,047,993 B2 * | 11/2011 | Shau | A61B 8/08 382/128 |
| 8,068,650 B2 | 11/2011 | Kumar et al. | |

(Continued)

OTHER PUBLICATIONS

"Algorithms for radiological image registration and their clinical application", Hawkes et al, (J. Anat. (1998) 193, pp. 347-361).

(Continued)

*Primary Examiner* — Tsung-Yin Tsai

(57) ABSTRACT

A system and method for automatic detection of an object feature, such as a lesion, across a plurality of sets of image data, taken from the same subject, which may optionally be a human patient but which may also optionally be any type of animal or a non-biological subject.

19 Claims, 6 Drawing Sheets

(56) References Cited

U.S. PATENT DOCUMENTS

| | | | | |
|---|---|---|---|---|
| 8,073,226 | B2* | 12/2011 | Farag | G06K 9/0014 |
| | | | | 378/21 |
| 8,194,964 | B2* | 6/2012 | Wiley | G06T 7/0014 |
| | | | | 382/131 |
| 8,644,578 | B1* | 2/2014 | Wiley | G06T 7/0085 |
| | | | | 382/131 |
| 2004/0223636 | A1* | 11/2004 | Edic | G06T 7/0012 |
| | | | | 382/131 |
| 2006/0025669 | A1* | 2/2006 | Ramamurthy | G06T 5/50 |
| | | | | 600/407 |
| 2008/0260222 | A1* | 10/2008 | Kumar | A61B 6/032 |
| | | | | 382/128 |
| 2009/0220137 | A1* | 9/2009 | Chefd'hotel | G06T 7/0081 |
| | | | | 382/131 |
| 2009/0279754 | A1 | 11/2009 | Gindele et al. | |
| 2010/0091035 | A1* | 4/2010 | Kirchberg | G06K 9/342 |
| | | | | 345/620 |
| 2010/0128954 | A1* | 5/2010 | Ostrovsky-Berman | G06T 7/0081 |
| | | | | 382/131 |
| 2010/0235352 | A1 | 9/2010 | Slutsky et al. | |
| 2010/0254584 | A1 | 10/2010 | Gulsun et al. | |
| 2010/0266170 | A1 | 10/2010 | Khamene et al. | |

OTHER PUBLICATIONS

"Image registration: an essential tool for nuclear medicine", Hutton et al (Eur J Nucl Med (2002) 29: pp. 559-577).
International Search Report completed Jun. 28, 2012 for International Application No. PCT/US12/32341, 2 Pages.
U.S. Appl. No. 12/823,346, filed Jun. 25, 2010, Simon.
Helen Hong et al., "Automatic lung nodule matching on sequential CT images", Computers in Biology and Medicine, Vil. 38, 2008, pp. 623-634.
Supplemental European Search Report for Application No. EP 12 76 8069, dated Nov. 5, 2014, 2 pages.

\* cited by examiner

IMAGE ANALYSIS FOR SPECIFIC OBJECTS

CROSS REFERENCE TO RELATED APPLICATIONS

This application claims the benefit of and is a US national phase filing of PCT application No. PCT/US12/32341 filed Apr. 5, 2012 that is entitled, "IMAGE ANALYSIS FOR SPECIFIC OBJECTS", in the names of Tiferet T. Gazit, Yosef Y. Markov, Uri U. Einav, Hadas H. Padan and Guy E. Engelhard; which itself claims benefit of Provisional application U.S. Ser. No. 61/473,250, provisionally filed on Apr. 8, 2011 that is entitled, "IMAGE ANALYSIS FOR SPECIFIC OBJECTS", in the names of Tiferet T. Gazit, Yosef Y. Markov, Uri U. Einav and Hadas H. Padan; the disclosures of both priority applications are incorporated herein by reference in their entirety.

FIELD OF THE INVENTION

The present invention relates to a system and method for identification, analysis, and comparison of specific objects in image data and particularly, but not exclusively, to automatic lesion segmentation and comparison in image data of bodily tissue and/or object feature analysis in image data from non-biological subjects.

BACKGROUND OF THE INVENTION

Image segmentation is the problem of extracting or "segmenting" objects of interest from non-interesting background information in an image. Reliable image segmentation algorithms are required in many fields, particularly for medical images such as CT (computerized tomography) scans, MRI (magnetic resonance imaging) scans, PET (positron emission tomography) scans and the like. For the field of medical image processing, it is important to be able to accurately, rapidly and reliably perform segmentation, as medical diagnoses increasingly rely upon such information. As a non-limiting example, detection and determination of various physical parameters of lesions, such as volume, longest diameter and so forth, are important for the diagnosis of many diseases. In addition, determination of the growth rate of such lesions is also important for disease diagnosis and prognosis.

Fully automatic image segmentation has so far proven to be impractical and unreliable, particularly for three dimensional images such as those which arise from the above described scans. These three dimensional images are provided as a series of two dimensional slices; image segmentation algorithms must therefore relate to both individual two dimensional slices and to the overall three dimensional construct that is composed of a plurality of such slices. Therefore, many currently available medical image processing algorithms rely upon a mixture of automated and manual algorithms, which require human interaction with the medical image data.

Certain algorithms are available for performing such segmentation which only require minimal user input, including for example those algorithms taught in U.S. Pat. No. 7,773,791 to Simon et al, filed on Dec. 7, 2006, issued on Aug. 10, 2010; U.S. Pat. No. 7,844,087 to Ray et al, filed on Dec. 19, 2006, issued on Nov. 30, 2010; US Patent Application No. 20090279754 to Gindele et al, filed on Dec. 22, 2008, published on Nov. 12, 2009; and U.S. patent application Ser. No. 12/823,346 to Simon, filed on Jun. 25, 2010; all of which are, hereby incorporated by reference as if fully set forth herein. These algorithms require only minimal inputs, such as a single point in the lesion or a line corresponding to a long diameter, which are typically entered by the user, for example by indicating or "clicking on" a point on and/or in an image of a lesion with a mouse or other pointing device through a computer display of such an image. Given such inputs these algorithms compute a 3D (three dimensional) segmentation of the lesion as well as a longest diameter and a second diameter. These diameters form part of the diagnostic standard of care as determined for example by the RECIST (response evaluation criteria in solid tumors) and WHO (World Health Organization) guidelines. However, as such lesion measurements are inherently inaccurate, given that they rely upon only linear measurements, optionally and preferably lesion volume is calculated as described herein through segmentation, which is more accurate. The determination of lesion volume over time is also an important diagnostic tool, which is more accurately performed through comparisons between segmented lesions in 3D image data at a plurality of time points.

Currently available tools, such as the PACS system from Carestream Healthcare Inc (USA); as presented during the RSNA meeting of November 2010, display the segmented lesion contours within a user display, along with the volume and diameter measurements and the lines representing the diameters. In order not to hide the data, the diameter lines and/or the lesion contours may optionally appear only when the user hovers over a given lesion. The system also automatically adds these measurements to the radiology report. It further allows grouping of lesions across different studies (image data acquired on different dates) of the same patient, and automatically computes growth rate and doubling time for such grouped lesions in the report. However, the system currently requires the lesions to be determined at least partially according to user input as described above in all the relevant studies before such grouping may be performed.

SUMMARY OF THE INVENTION

The background art describe methods to transform a lesion from a source image to a target image using a registration of the source and target followed by the transformation of the segmented lesion from the source image to the target image using the calculated registration matrix but does not relate to automatic detection of lesions across a plurality of sets of image data taken from the same subject in which this registration cannot align the lesion in the plurality of data sets.

The present invention overcomes the above drawbacks of the background art by providing a system and method for automatic detection of lesions across a plurality of sets of image data taken from the same subject, in which a registration cannot align the lesion in the plurality of data sets. Optionally, the registration cannot align the lesion in the plurality of data sets because the output of the prior registration is a registration matrix whose degrees of freedom only allow for combinations of rotations, translations, scaling and shearing transformations. Optionally, additionally or alternatively, the registration cannot align the lesion in the plurality of data sets because the lesion has changed shape such that the prior registration cannot be applied to the lesion with the changed shape using a combination of only rotations, translations, scaling and shearing.

As used herein, the term "lesion" may also optionally encompass any type of object feature in an animal, preferably a mammal, which changes over time. Such object features may optionally include but are not limited to any type of organ or tissue or pathology. Changing over time may optionally encompass growing or shrinking, changing in density or texture, or changing in shape, for example, with regard to the organ or tissue or pathology. Non-biological object features are also considered to be encompassed within at least some embodiments of the present invention.

If the output of the registration is a registration matrix, then the available transformations for a lesion between different sets of data are limited to only rotations, translations, scaling and shearing. If the shape of lesion is different in the different sets of data in any other way, then the registration matrix cannot be used. This problem may also optionally be described such that the registration cannot align the lesion in the plurality of data sets because the lesion has changed shape such that the registration cannot be applied to the lesion with the changed shape with a combination of only rotations, translations, scaling and shearing (regardless of the exact type of registration).

These specific changes (rotations, translations, scaling and shearing) are the only changes that can be modeled by the nine degrees of freedom in a registration matrix, whereas the system and method as described herein allow for arbitrary transformations, including for example and without limitations, changes to the shape of the lesion including, for example, growing a new lobe.

Without wishing to be limited in any way, as a non-limiting example of a medical scenario in which the ability to apply arbitrary transformations becomes important, it is possible that image data is taken at separated time points (for example, image data taken a few months apart), for the purpose of evaluating disease progression. In this scenario, the lesions are expected to change significantly in both size and shape, undergoing anisotropic growth or cell death and sometimes even merging with other nearby lesions, and in such cases the art known methods would be of little use.

Some art known systems are able to handle image data from different types of imaging modalities, as for example described in U.S. Pat. No. 8,068,650 to Kumar Shashi et al, issued on Nov. 29, 2011. Other art known systems are stated to be able to handle imaging data on lesions taken over time, but all of these systems are limited to registrations that have a registration matrix as an output and hence, as described above, are limited in their potential transformations (see for example U.S. Pat. No. 8,068,650 and U.S. Pat. No. 6,373,998 to Thirion, Jean-Philippe et al, issued on Apr. 16, 2002). Thus, none of the art known systems relates to the above capabilities of the method and system of the present invention.

According to at least some embodiments, a lesion of interest is first detected in a first or source set of image data. The term "image data" as used herein relates to two or three dimensional image data unless otherwise indicated. Optionally adjustments are made to the below methods according to the type of data, such that for example for two dimensional image data, area calculations are performed rather than volume calculations. Optionally, temporal data may also be used, such as a video stream of two or three dimensional data, including but not limited to from ultrasound or from cardiac MRI (the latter is used for example for viewing functionality of the heart). Once the lesion of interest has been detected, and its borders determined, then one or more additional sets of image data are analyzed to determine whether the lesion is present in such one or more sets of data, which may optionally be termed "target set(s) of data" as described herein. If detected, the lesion is segmented, and one or more parameters of the lesion are optionally determined, including but not limited to longest diameter, second diameter, lesion volume, and/or average Hounsefield values.

According to at least some embodiments of the present invention, the method optionally uses segmentation analysis of a lesion in one set of data, such as a study at a particular time point (date) to automatically compute the segmentation of the same lesion in a different study of the same subject, preferably by using a known registration method, non-limiting examples of which are described with regard to "Algorithms for radiological image registration and their clinical application" by Hawkes et al (J. Anat. (1998) 193, pp. 347-361); "Image registration: an essential tool for nuclear medicine" by Hutton et al (Eur J Nucl Med (2002) 29: pp 559-577); and US Patent Application No. 20100235352; all of which are hereby incorporated by reference as if fully set forth herein. Of course, other registration methods could also optionally be used in place of, or in addition to, the methods described in these papers. This method can also compute a lesion in a prior study from the segmentation in the current study or vice versa, and is very robust to any changes in the lesion, including but not limited to any one or more of dramatic lesion growth, shrinkage, calcification, and other changes in shape or density. For example and without wishing to be limited in any way, optionally segmentation for at least one other set of image data may be performed based upon a previously determined segmentation of a lesion in a set of image data. Alternatively or additionally, a plurality of sets of image data that are not segmented are provided; after segmentation of the lesion is performed for one set of image data, such segmentation may optionally be automatically performed for at least one other set of image data (or all sets of image data).

According to at least some embodiments of the present invention, any suitable method for segmenting an object feature such as a lesion in imaging data taken from a subject, such as a human subject for example, may be incorporated into the below described methods. Similarly, any suitable registration method may also optionally be incorporated. As used herein, the term "refined registration method" optionally and preferably refers to a method that provides a locally accurate registration about a predefined location, such as (for example and without limitation) a user defined location.

As non-limiting illustrative examples for discussion purposes only, two methods according to at least some embodiments of the present invention are discussed below, corresponding to two reading workflows that may be used for example by radiologists. These workflows relate to embodiments in which some type of initial user (manual) input forms the basis for the operation of the method, although of course such methods could also optionally be extrapolated to automatic workflows, also as described herein. In this example, reference is made to "patients" as non-limiting examples, which are typically human subjects. The first workflow is primarily relevant in cases where a radiologist is asked to read a current patient study for which history (prior studies from previous scanning dates) is available but lesions have not yet been segmented in any of the studies. In this case the radiologist will scan through one of the patient studies, manually locate lesions, and provide some minimal user input for each lesion in this study, such as a click within the lesion or a line corresponding to the longest diameter of the lesion. From this input on a single study, a method according to at least some embodiments of the present invention automatically segments each such lesion in all relevant sets of image data from this patient, across different study dates. As part of this process the method preferably incorporates performing a refined registration for all these studies based on the location of the user's input, so that the studies will be better aligned locally in this region of interest, thereby helping the radiologist visually inspect the results. Optionally, the groupings of equivalent lesions across different sets of image data are saved, for example for future computing of quantitative measures of lesion change over time, such as growth rate and doubling time.

The second workflow is initiated from a single set of image data in which one or more lesions have already been segmented, and is primarily but not exclusively relevant in cases where a radiologist is asked to read a current patient study in which lesions have not yet been segmented and for which at least one prior set of image data is available in which one or more lesions have already been segmented. Typically the lesions in the prior study would have been segmented upon the radiologist's reading of that prior study in a prior date, shortly after that scan was taken. In this case the method according to at least some embodiments optionally automatically reviews one or more lesions segmented in the initial study (optionally all such lesions are reviewed), and segments and groups the equivalent lesions in one or more other relevant sets of image data. Optionally, the lesions may be reviewed in all such relevant sets of image data. In any case, the method again optionally computes quantitative measures of lesion change over time.

Without wishing to be limited by a closed list, these methods can significantly impact reading time, for example by saving time that would otherwise be required for searching for a lesion in multiple studies of a subject. In addition (and also without wishing to be limited by a closed list), by making it fast and easy to accurately measure volumetric changes in lesions over time, these methods may impact patient care and outcomes, for example by decreasing the percent change in a lesion necessary to determine the nature of the disease and the effectiveness of a current treatment. Additionally, these semi-automatic methods improve the robustness of the measurement process, making the quoted values independent of the radiologists that read them. Additionally, by automatically including such measurements into the report, more time is saved for the radiologist.

Without wishing to be limited in any way, optionally the above method may be used for lesions in various body tissues and organs of the subject, for example including but not limited to the lungs, liver, bones, uterus, prostate, ovaries, breasts, brain, stomach (or indeed any portion of the gastrointestinal tract, including the mouth and/or esophagus), lymph nodes, colon, pancreas or any suitable soft tissues. Furthermore, optionally a plurality of targets (a plurality of lesions) may be segmented according to various embodiments of the present invention.

Without wishing to be limited in any way, optionally the above method may be used for lesions across various modalities and different types of image data, including but not limited to CT, MRI, PET scan data and so forth, and optionally to correlate data between these different types of image data.

Although the present description centers around medical image data, it is understood that the present invention may optionally be applied to any suitable image data, optionally including temporal data such as video streams, including but not limited to computer games, graphics, artificial vision, computer animation, biological modeling (including without limitation tumor modeling) and the like.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Although the present invention is described with regard to a "computer" on a "computer network", it should be noted that optionally any device featuring a data processor and the ability to execute one or more instructions may be described as a computer, including but not limited to any type of personal computer (PC), a server, a cellular telephone, an IP telephone, a smart phone, a PDA (personal digital assistant), or a pager. Any two or more of such devices in communication with each other may optionally comprise a "computer network".

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DESCRIPTION OF AT LEAST SOME EMBODIMENTS OF THE INVENTION

This application claims priority to U.S. Provisional Patent Application No. 61/473,250 filed Apr. 8, 2011, entitled "IMAGE ANALYSIS FOR SPECIFIC OBJECTS" to Einav et al.

At least some embodiments of the present invention are now described with regard to the following illustrations and accompanying description, which are not intended to be limiting in any way.

Figure 1:
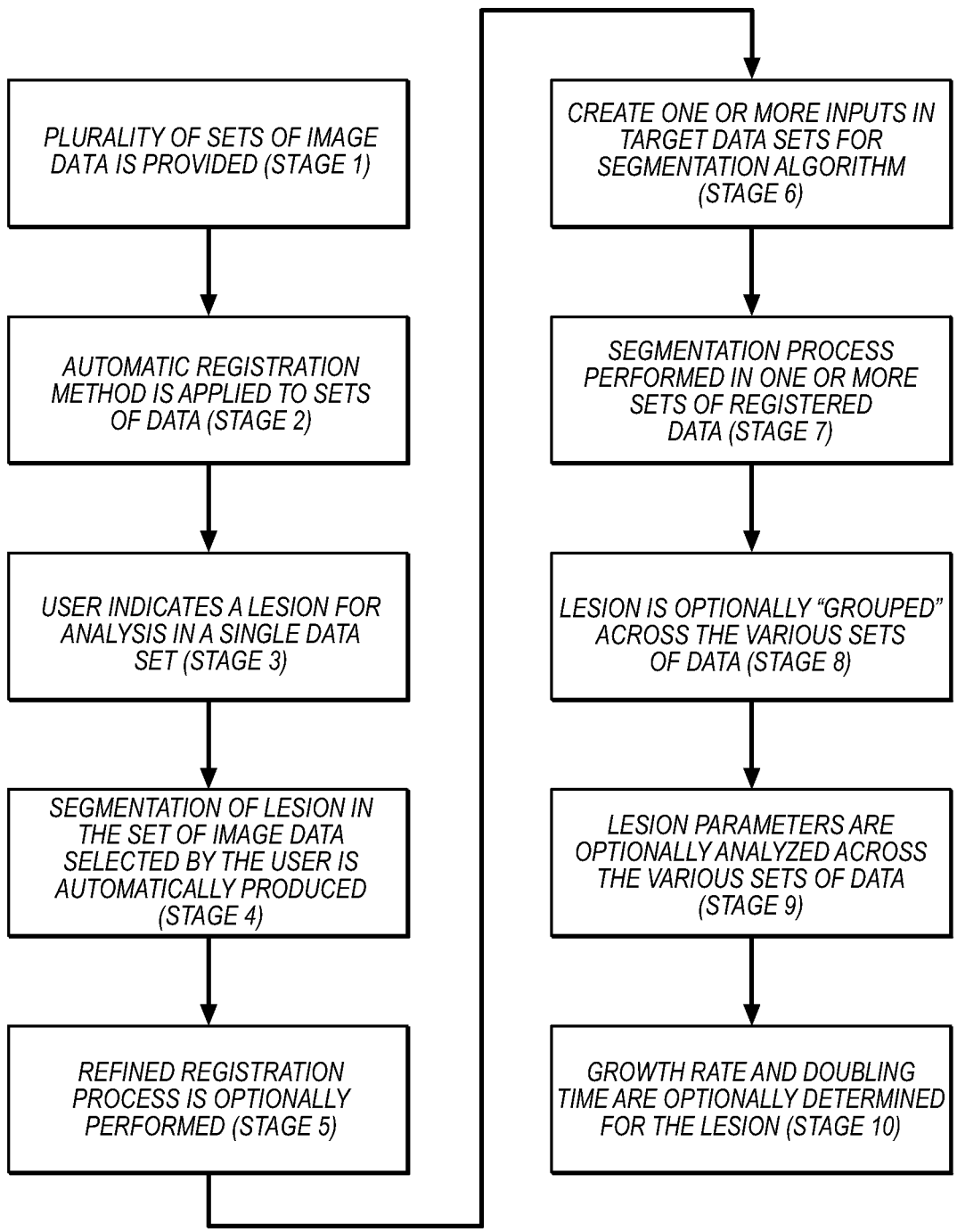
FIG. 1 shows an exemplary, illustrative method for automatic detection of a lesion in a plurality of sets of image data according to at least some embodiments of the present invention.

Referring now to the drawings, FIG. 1 shows an exemplary, illustrative method for automatic detection of a lesion in a plurality of sets of image data according to at least some embodiments of the present invention. In stage 1, a plurality of sets of image data related to a subject are provided. The provision may optionally be made through user selection for example, and/or may optionally be made automatically, for example according to various parameters in the DICOM. For this method, it is assumed that none of the sets of image data have been segmented, or optionally that no existing segmentations are used. Optionally, the different sets of image data relate to different studies, which are different sets of image data collected at different time points, typically on different dates. Optionally the studies come from different modalities and types of image data as previously described. In stage 2, any suitable automatic registration method, such as for example and without limitation the previously described automatic registration method, is applied to all of the different sets of data.

In stage 3, the user optionally indicates a lesion for analysis in a single one of the sets of image data, for example by selecting or "clicking on" a point within the lesion or drawing a line defining a lesion diameter with a mouse or other pointing device as described previously, although optionally any method for indicating a lesion may be used as is known in the art. For example, in the previously described PACS system, a lesion in the lung may optionally be indicated by a "click" by the user anywhere in the lesion itself. However, it should be noted that this stage is optional and that instead the lesion may optionally be selected automatically. Optionally, a different segmentation algorithm may be used depending on the modality and/or body location; for example, one segmentation algorithm may optionally be selected as suitable for segmenting a lung lesion in a CT, while another, different segmentation algorithm may optionally be selected as suitable for segmenting a brain lesion on MRI data.

In stage 4, a segmentation of this lesion in the data set selected by the user is automatically produced according to a suitable algorithm for segmenting a lesion, such as for example and without limitation the previously described segmentation methods. In stage 5 (although optionally performed in parallel with stage 4), a refined registration process is preferably performed for all of the sets of data. The refined registration process optimizes the registration between the various sets of data for a local region that is based on the location of the user's input or inputs by taking a single point in one set of data and finding a transformation that will align this set of data with one or more other sets of data from the same subject, where the transformation will cause the region around the input point to be particularly accurately aligned as previously described. After this process is performed, the image data in these different sets of data is better aligned locally in the region of interest.

Figure 3A:
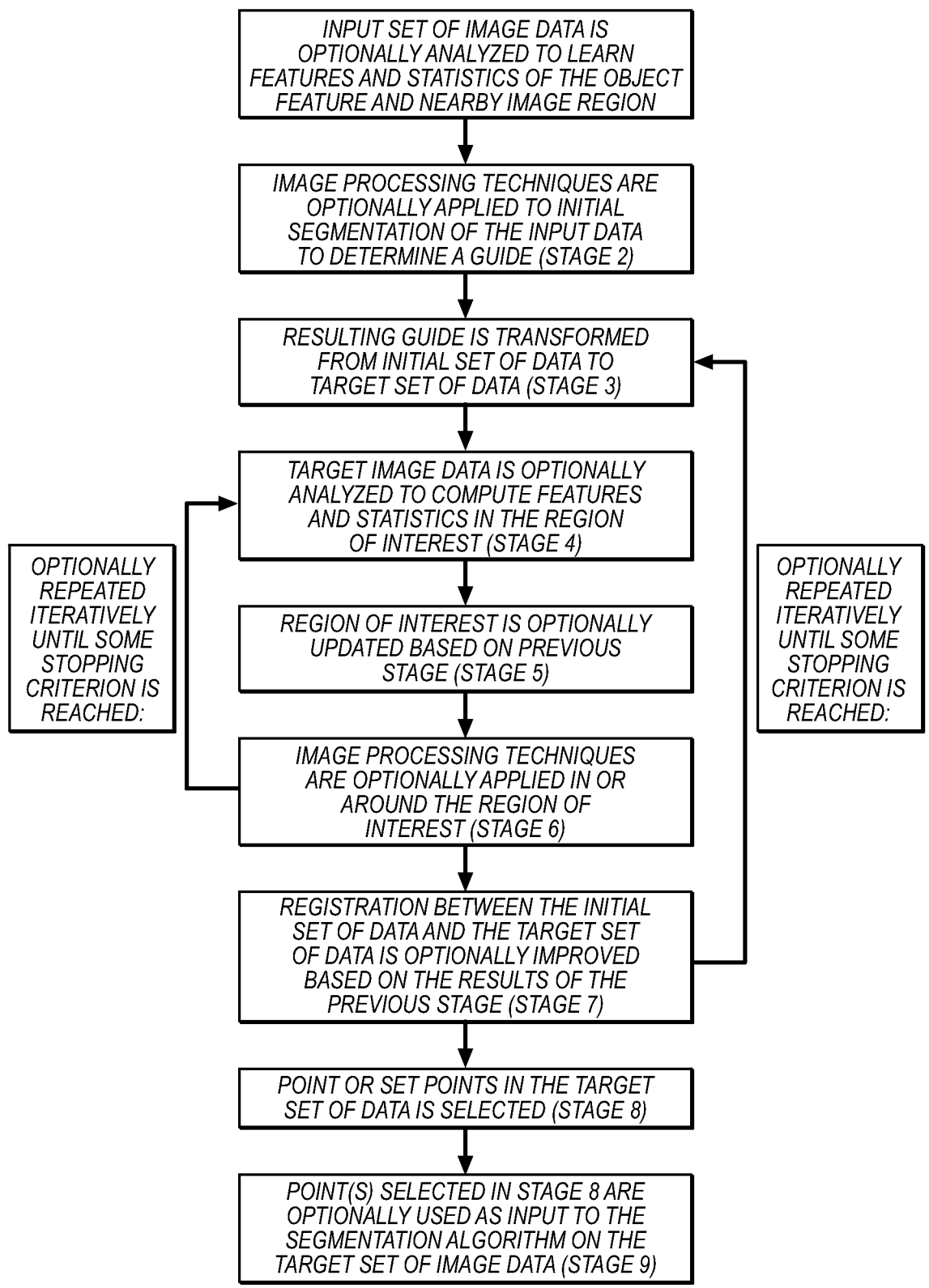
FIGS. 3A-3C show exemplary, illustrative non-limiting methods for automatically determining an input for object feature segmentation in a plurality of sets of image data according to at least some embodiments of the present invention, in which FIG. 3A relates to a more general method while FIG. 3B relates to such input determination for lesions in lung tissue image data and FIG. 3C relates to such input determination for lesions in liver tissue image data.
Figure 3B:
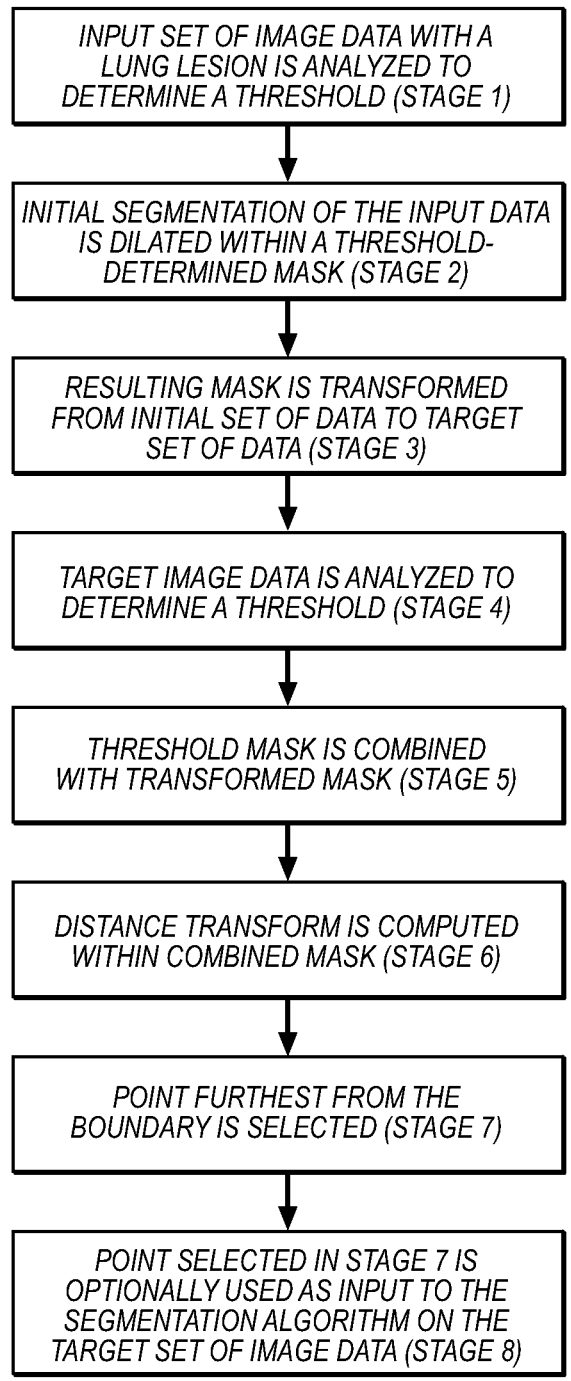
Figure 3C:
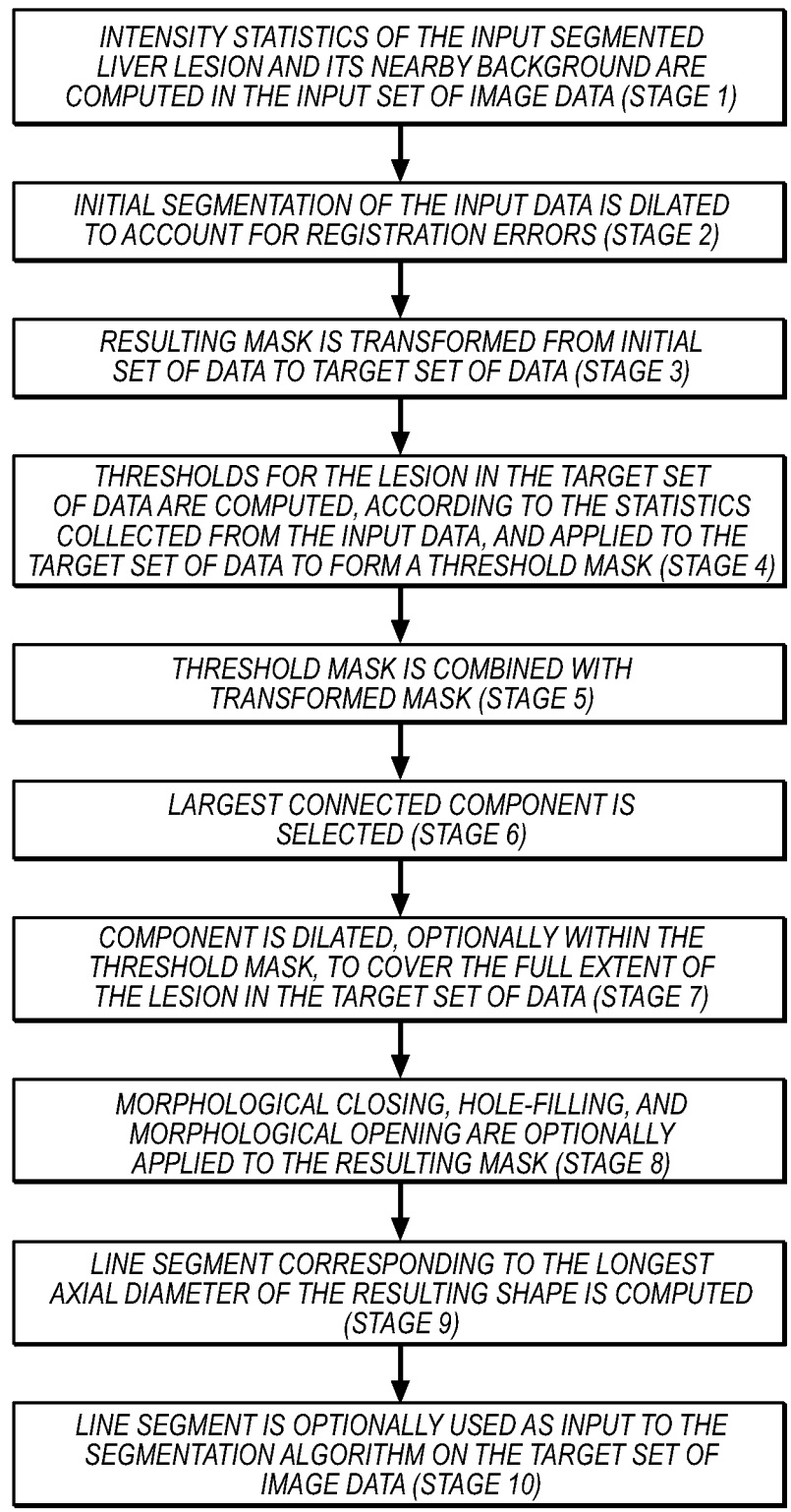

In stage 6, one or more inputs in the target data sets for the segmentation algorithm are determined, as described in more detail with regard to FIGS. 3A-3C.

In stage 7, the segmentation process is performed on each target data set, optionally according to the input found in the previous stage. Optionally, however, the segmentation process performed in stages 4 and 7 is different. Optionally and preferably, additional input information is used in order to select a segmentation process. The additional input information may optionally relate to a different type of imaging data and/or to a particular tissue location for the data being segmented, such as lung versus liver, for example. For example, there may be optionally two different types of input imaging data, such as CT data and MRI data, or even two dimensional x-ray data. If a lesion, such as a lung lesion for example, is being examined, then the type of algorithm selected may optionally depend on the identification of the tissue of lesion and/or of the type of image data.

For example, this hypothetical lung lesion may optionally be detected in the CT data (whether automatically or through manual segmentation and identification), and then transferred to MRI data; however, it is possible that different segmentation algorithms would be used for the two different types of imaging data; furthermore, the selection may also optionally depend upon the identification of the tissue as "lung". Upon provision of MRI imaging data of the lung as the target data set, optionally the MRI lung lesion segmentation algorithm may be selected. Of course, such a process may optionally be performed for different types of tissue, including but not limited to liver, brain, kidneys, lymph nodes, breast and so forth.

Once segmentation has been performed across the plurality of sets of data, the lesion is preferably "grouped" across the various sets of data, such that the lesion is preferably identified as such in all sets of data, in stage 8. Based upon such grouping, the lesion parameters are preferably analyzed across all sets of data in stage 9. Such lesion parameters preferably include but are not limited to one or more of longest diameter, a second diameter, and/or lesion volume (for two dimensional image data, lesion area would be calculated); for CT data, average Hounsfield units (HU) may also optionally be calculated. In stage 10, the growth rate and/or doubling time for the lesion are preferably determined from these parameters, assuming that the different sets of image data relate to image data from the same subject taken over a plurality of different time points. These parameters and measures of growth can be automatically exported to a report, which may for example optionally be generated by and stored in the previously described PACS system, or sent to the RIS (radiology information system) or HIS (hospital information system), or any other such electronic record keeping system, for further analysis by other physicians in order to determine the course of treatment.

Stages 5-10 of this figure may optionally be performed in parallel for multiple target data sets.

Any one or more of the images of the detected lesion within one or more sets of image data, one or more lesion parameters and/or the growth rate and/or the doubling time may optionally be displayed to the user at any time, whether through a computer display (for example, as part of the previously described PACS system) and/or through a report or other provision of data to the user.

Figure 2:
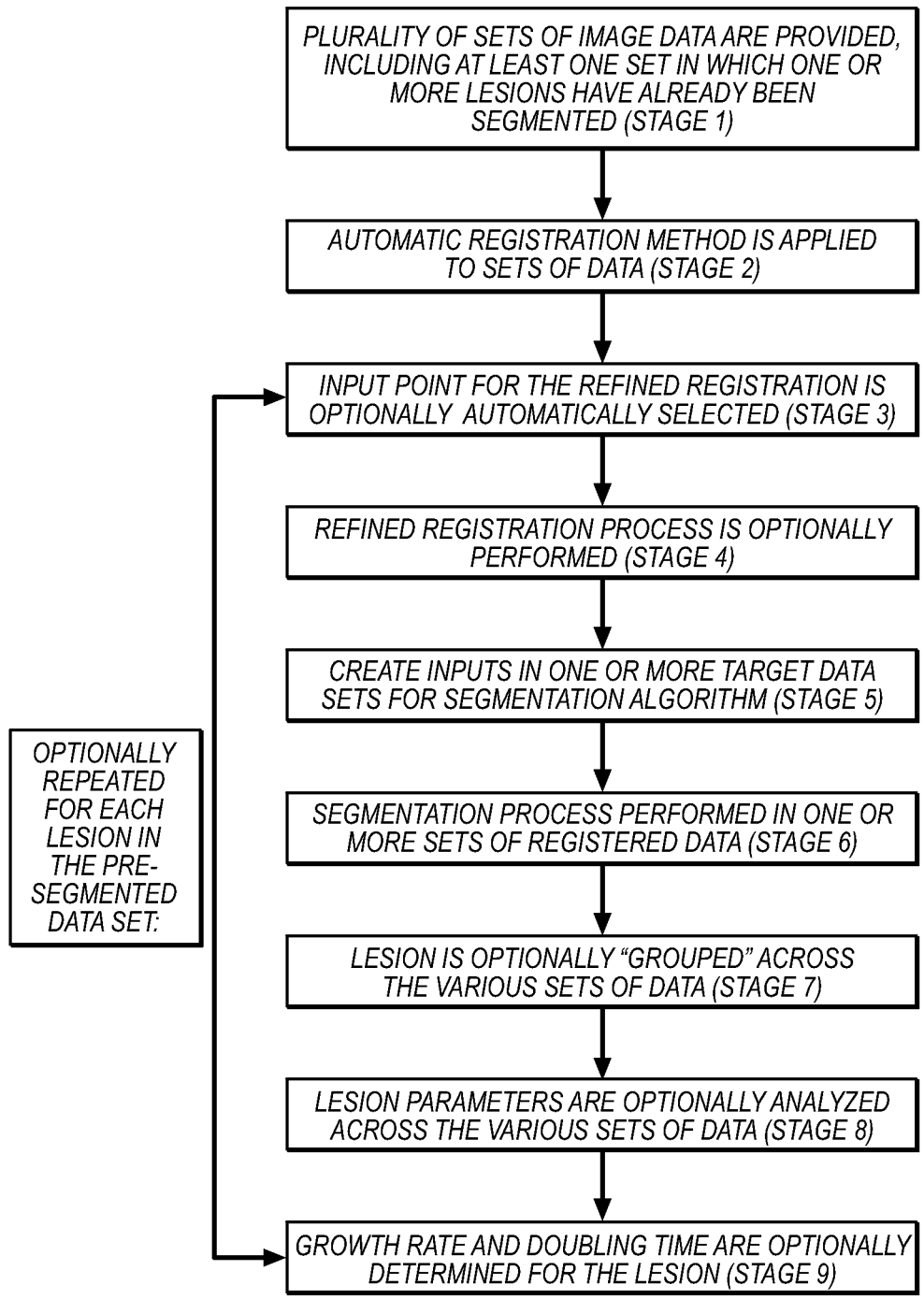
FIG. 2 shows another exemplary, illustrative method for automatic detection of a lesion in a plurality of sets of image data, in which at least one set of image data has been previously segmented, according to at least some embodiments of the present invention.

FIG. 2 shows another exemplary, illustrative method for automatic detection of a lesion in a plurality of sets of image data, in which at least one set of image data has been previously segmented, for example during a radiologist's reading of the data on a prior scanning date, according to at least some embodiments of the present invention. Optionally, the method of FIG. 2 may be performed for each of the lesions in the previously segmented study, whether serially or in parallel, such that all lesions in the prior study are now segmented automatically in the rest of the studies. In stage 1, a plurality of sets of image data related to a subject are provided. For this method, it is assumed that at least one set of image data has been segmented and that one or more lesions have been detected in the segmented image data. Optionally, the different sets of image data relate to different studies, which are different sets of image data collected at different time points, typically on different dates. Optionally the studies come from different modalities and/or types of image data as previously described. In stage 2, the previously described automatic registration method is applied to all of the different sets of data as previously described.

The rest of the stages described below are optionally and preferably repeated for each of the lesions in the pre-segmented set of image data (also referred to as the initial data set). If the initial data set contained multiple lesions, the stages described below may optionally be performed for all lesions in parallel.

In stage 3, the input point for the refined registration is preferably automatically selected from the existing segmentation, using for example the center of the lesion or the center of the lesion's longest diameter, or if stored, optionally by using the original click point or other user input used in segmenting this lesion. In stage 4, a refined registration process is preferably performed for all of the relevant sets of data as previously described.

In stage 5, one or more inputs in the target data sets for the segmentation algorithm are determined, optionally as described in greater detail with regard to FIGS. 3A-C. In stage 6, the segmentation process is performed on one or more target data sets according to the input found in the previous stage. It should be noted that a segmentation process may optionally be selected at this point according to additional input information, such as the identification of the type of imaging input data, as described with regard to stage 7 of FIG. 1 in more detail.

Once segmentation has been performed across the plurality of sets of data, the lesion is preferably "grouped" across the various sets of data, such that the lesion is preferably identified as such in all sets of data, in stage 7 as previously described. Based upon such grouping, the lesion parameters are preferably analyzed across one or more, or more preferably all, sets of data in stage 8 as previously described. Such lesion parameters preferably include but are not limited to one or more of longest diameter, a second diameter, and/or lesion volume (for three dimensional data; for two dimensional data, lesion area would be substituted).

In stage 9, the growth rate and/or doubling time for the lesion are preferably determined from these parameters, assuming that the different sets of image data relate to image data from the same subject taken over a plurality of different time points, again as previously described. These parameters and measures of growth can be automatically exported to a report, which may for example optionally be generated by and stored in the previously described PACS system, or sent to the RIS or HIS (or any other electronic record keeping system) for further analysis by other physicians in order to determine the course of treatment. Stages 3-9 are optionally performed for each lesion in the pre-segmented data set.

As described for FIG. 1 above, any one or more of the image of the detected lesion within one or more sets of image data, one or more lesion parameters and/or the growth rate and/or the doubling time may optionally be displayed to the user at any time, whether through a computer display (for example, as part of the previously described PACS system) and/or through a report or other provision of data to the user.

For the method of FIG. 1, the segmentation algorithm of stage 4 may optionally receive or even require some type of input, including but not limited to one or more "clicks" or user indications of points on and/or in the lesion with a mouse or other pointing device by the user through a computer display of the image data to the user, as previously described, although of course other types of segmentation algorithms could be used in addition to or in place of such an algorithm. Preferably the method of FIG. 2 is performed without such user inputs.

Also for both of the methods of FIGS. 1 and 2, the user may optionally indicate in which sets of data the lesion is to be segmented. Alternately, one or more sets of data may optionally be selected automatically (for example, including but not limited to all studies or sets of data from a specific subject, all studies currently displayed on the screen, all studies the user chose to register together, or a combination thereof). Automatic selection may additionally be based on parsing of DICOM (Digital Imaging and Communications in Medicine standard) tags and display protocol (hanging protocols). For example and without wishing to be limited, the method may optionally be applied to all studies of the same modality from the same subject to which the user has applied the automatic registration and that are currently displayed on the screen.

FIGS. 3A-3C show optional exemplary, illustrative methods for determining one or more inputs for segmentation of an object feature, such as a lesion, in a plurality of sets of image data according to at least some embodiments of the present invention. These embodiments of the methods also relate to the input employed for automatic segmentation of an object feature, such as a lesion, in a second or target set of image data, given that the object feature has been segmented in a first or input set of image data. The methods use the object feature segmentation in one set of image data to fully-automatically compute the segmentation of the same object feature in a different data set of the same subject (for example, the same patient). FIG. 3A relates to a general method, while FIG. 3B relates to a specific method performed on lesions in lung image data and FIG. 3C relates to a specific method performed on lesions in liver image data. Although FIG. 3B is described herein with regard to lung image data as a non-limiting example only, while FIG. 3C is described herein with regard to liver image data as a non-limiting example only, the method may optionally be broadened to relate to any type of image data, optionally (but not exclusively) tissue image data. Furthermore, FIG. 3A may optionally be performed with regard to any type of image data as previously described (two dimensional, three dimensional, temporal and so forth). FIGS. 3B and 3C as described relate to three dimensional image data but could easily be adapted by one of ordinary skill in the art to any other type of image data as described herein.

All of these figures relate to methods which optionally and preferably incorporate determination of the registration between a plurality of sets of image data, as computed for example in stages 2 and 5 of FIG. 1, with information from the segmented object feature, such as a lesion, in the initial data set, as computed for example in stage 4 of FIG. 1, in order to find a point or set of points in the target data set that may optionally serve as input for a segmentation algorithm of the same type as was used in stage 4 of FIG. 1.

FIG. 3A as shown relates to an optional exemplary, illustrative method for determining an input for segmentation in a plurality of sets of image data according to at least some embodiments of the present invention for general application. As shown, in stage 1, the input set of image data is optionally analyzed to learn features and statistics of the object feature and nearby image region.

In stage 2, image processing techniques are optionally applied to the initial segmentation of the input data for determining a guide for later stages. Such a guide may optionally comprise one or more of a resulting point or set of points, and/or a mask and/or a probability map regarding the segmentation of the lesion in the input image data.

In stage 3, the resulting guide is transformed from the initial set of image data to the target set of image data, optionally and preferably by using the transformation specified by the previously described refined registration process.

In stage 4, the target image data is optionally analyzed to compute features and statistics in the region of interest, which may optionally be indicated by the transformed guide in the first iteration. Additionally or alternatively, if stages 4-6 are performed iteratively, the region of interest may be determined according to the results of stage 6, after at least one iteration has been performed.

In stage 5, the region of interest is optionally updated according to the results of stage 4. In stage 6, image processing techniques are optionally applied in or around the region of interest. Stages 4-6 are optionally repeated iteratively until some stopping criterion is reached, such as, for example, a predetermined number of iterations, a satisfactory score on some measure of goodness-of-fit between the data and the current region of interest, and/or a reduction of a delta to the region of interest between successive iterations such that it falls below a certain threshold.

In stage 7, registration between the initial set of data and the target set of data is optionally improved based on the results of the previous stage. Stages 3-7 are optionally repeated iteratively until some stopping criterion is reached, such as, for example, the stopping criteria listed in stage 6 above.

In stage 8, one or more points are selected in the target set of data according to the previously performed processing results and optionally the improved registration. In stage 9, the one or more points selected in this manner become the input to the segmentation algorithm on the target set of image data, for example as previously described with regard to FIGS. 1 and 2.

Turning now to FIG. 3B, which is a specific non-limiting example of the method of FIG. 3A for lesions in lung image data (such as CT data for example), in stage 1, the input set of image data is optionally analyzed to determine a threshold that selects only low-intensity voxels (data points); the voxels selected are preferably in the lung parenchyma but not in lesions, blood vessels, or the pleural wall. The threshold may optionally be automatically determined according to a histogram of a ROI (region of interest) about the lesion, possibly excluding the lesion itself. Alternatively, the histogram may optionally be constructed for a ROI that includes the lesion and also the lung parenchyma, such that two peaks are detected in the histogram according to each of these locations. Alternatively such a threshold could optionally be provided in advance.

In stage 2, the initial segmentation of the input data is dilated a plurality of times, but only within the mask created by this threshold, in order to create a larger image region about this initial segmentation in the input image data, in which to search for the lesion in the target study. Such a larger region may optionally be used in order to account for registration errors which might prevent the lesions in the two sets of data from overlapping after the transformation. However, dilation is preferably limited to a low intensity mask to prevent errors; for example, dilation is preferably limited so that the dilated region is not able to spread into the pleural wall, because the wall will be hard to differentiate from the lesion in the target study due to the high intensity of voxels related to the wall in the image data. Also, the input point selected for the segmentation in the target set of data preferably does not fall within the wall. Because the wall is a strong image feature in lung image data, it may be assumed that this feature would be well aligned locally by the refined registration. Another type of error, which is also prevented by limiting the dilation to a low-intensity mask, is the error of dilating a specific lesion to such an extent that it overlaps one or more other neighboring lesions, if such lesions exist. Since lesions have high intensity, the dilation would not be expected to enter neighboring lesions.

In stage 3, the resulting mask is transformed from the initial set of image data to the target set of image data using the transformation specified by the previously described refined registration process.

In stage 4, the target image data is analyzed to determine a threshold that selects relatively high intensity voxels; alternatively, such a threshold may optionally be previously determined. Again, the threshold may optionally be automatically determined as previously described. For example and without limitation, the threshold is preferably selected to include voxels belonging to lesions, blood vessels, and the pleural wall but to exclude the parenchyma; the latter tissue has relatively low intensity in comparison to the other tissues.

In stage 5, this threshold mask is combined with the transformed mask from stage 3 to form the combined mask. The combined mask includes the lesion and nearby blood vessels, but excludes both the parenchyma (due to the high-intensity threshold) and the pleural wall (barring major registration errors). In stage 6, a distance transform that takes into account the z-factor (ratio between in-slice and inter-slice image resolution) is computed within this combined mask. In stage 7, the point within the combined mask that lies furthest from the mask boundaries is selected. This point is expected fall within the lesion, except in rare cases where an error may occur; for example, such an error may occur if the lesion is tiny and is attached or very close to a blood vessel that is much thicker than the lesion. In stage 8, the point selected in this manner becomes the input to the segmentation algorithm on the target set of image data, for example as previously described with regard to FIGS. 1 and 2.

Turning now to FIG. 3C, which is a specific non-limiting example of the method of FIG. 3A for lesions in liver image data (such as CT data for example), the method described herein is relevant to a number of different types of liver lesions. The specific method is described as being performed on hypovascular lesions but may optionally be applied to hypervascular lesions by one of ordinary skill in the art, preferably with the assumption that the lesion is brighter rather than darker than the liver parenchyma. In stage 1, intensity statistics of the input segmented liver lesion and its nearby background are optionally and preferably computed for the input set of image data. For example, these intensity statistics could optionally comprise the intensity mean and STD (standard deviation) of the initial segmented lesion and its nearby background in the initial set of data. The nearby background is optionally defined as the voxels (data points) that lie within a small number of dilations of the segmented lesion, excluding the voxels belonging to the lesion itself, and preferably possessing intensities that are within the range that could belong to liver tissue (to exclude voxels lying in ribs or in the thoracic cavity neighboring the liver).

In stage 2, the initial segmentation of the input data is dilated to account for registration errors, forming a new mask. Preferably, the determination of the number of dilations to perform is related to the image resolution. The z-factor may also optionally be accounted for by optionally dilating a different number of times in-slice than in all three dimensions. Preferably, small lesions are dilated more than large lesions, since for small lesions even reasonable registration errors might prevent the transformed initial lesion from overlapping the target region fairly well.

In stage 3, the resulting mask is transformed from the initial set of data to the target set of data to form a transformed mask, preferably according to the refined registration. Optionally, stages 2 and 4 may be performed in any order. In stage 4, thresholds for the lesion in the target set of data are computed, according to the intensity statistics collected from the input data in stage 1, and applied to the target set of data to form a threshold mask. The thresholds for the lesion in the target study are preferably computed to select voxels that have intensities that are more likely to be lesion than background, according to the statistics computed from the initial lesion. Specifically but as a non-limiting optional example, an upper threshold is selected to define the intensity at which a voxel becomes more likely to be background than lesion (given a normal distribution of lesion and background intensities), and a lower threshold is selected that is either the lesion mean minus two STDs or the thoracic cavity upper threshold, whichever is higher.

In stage 5, the threshold mask is combined with the transformed mask to form a combined mask, by taking an intersection of the two masks.

In stage 6, the largest connected component is selected within the combined mask to form the core of the lesion in the target data set. In stage 7, this largest connected component is dilated to cover the full extent of the lesion in the target set of data. Preferably, this dilation is limited to spread only within another mask, optionally within the same threshold mask created in stage 4, to avoid leaks into liver parenchyma, blood vessels, regions lying outside the liver, and so on. Since this resulting shape is used to find the largest lesion diameter to use as input for the liver-lesion segmentation algorithm, it is important that this shape now cover the entire lesion in this target study. Preferably, the determination of the number of dilations to perform again takes into account the image resolution.

In stage 8, optionally one or more of the processes of morphological closing, hole-filling, and morphological opening are applied to the resulting mask determined after stages 6 and 7, to determine a final shape. Such methods may optionally be performed as described for example in Digital Image Processing, third edition, edited by Gonzalez and Woods; ISBN-13: 978-0131687288. Morphological closing is performed to include pockets of brighter voxels inside the lesion. Hole filling is performed to fill holes (connected-components of voxels labeled as background that are completely surrounded by lesion voxels and do not touch the main body of background voxels) in the lesion component to obtain a solid shape. Morphological opening is performed to obtain a smoother outer contour and remove any small irregularities extruding from the main body of the lesion. However, stage 8 is optionally not performed. In stage 9, the line segment corresponding to the longest axial diameter of the resulting shape from stages 7 and/or 8 is computed. In stage 10, the line segment is optionally used as input to the segmentation algorithm on the target set of image data.

Figure 4:
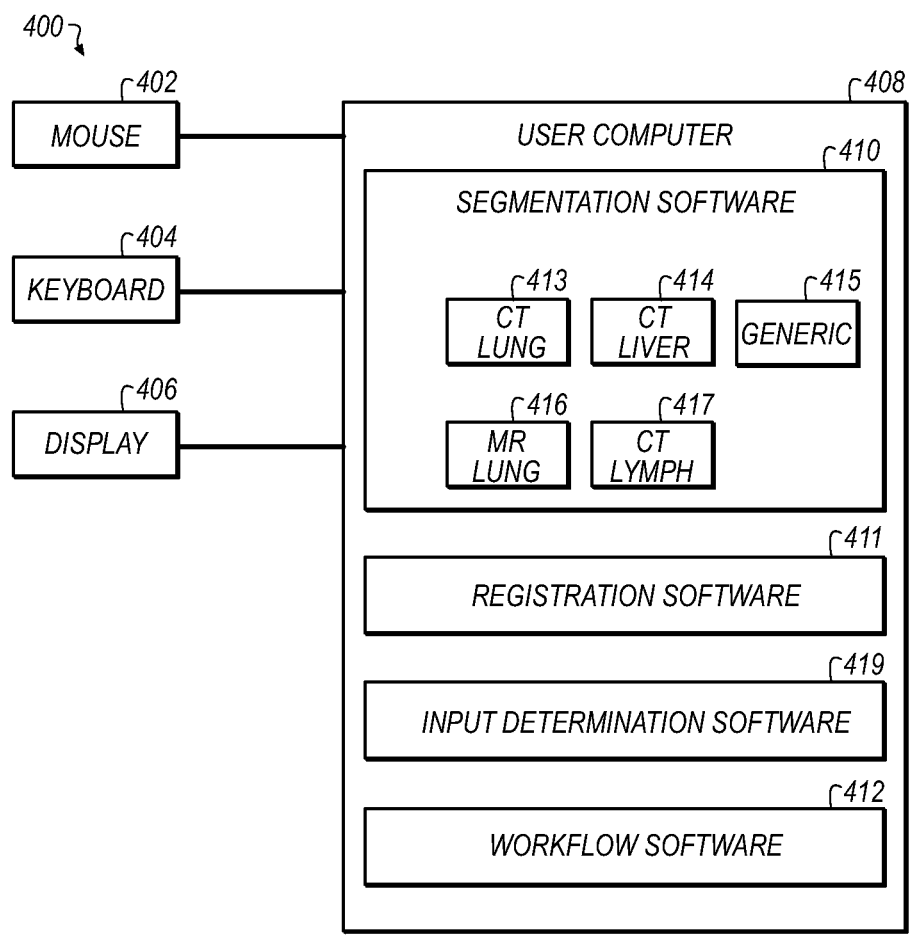
FIG. 4 shows an exemplary, non-limiting illustrative system according to at least some embodiments of the present invention.

FIG. 4 shows an exemplary, non-limiting illustrative system according to at least some embodiments of the present invention. As shown, a system 400 features a mouse 402 or other pointing device, a keyboard 404 and a display 406. Optionally any of these components may be combined, for example for a touch sensitive display screen; mouse 402 and keyboard 404 may optionally be described as an "input device". The user interacts with these components to perform the various methods as described herein where user interaction is indicated.

System 400 also features a user computer 408, which optionally comprise any computational device and which may optionally be a local or remote computer, and may optionally be a plurality of computers. User computer 408 operates a plurality of segmentation software modules, referred to collectively as segmentation software module 410. As described herein, optionally and preferably segmentation software module 410 may be implemented according to the art known methods described herein, more preferably according to the inventive variations and implementations described herein. Optionally and more preferably, segmentation software module 410 features a plurality of segmentation algorithms, for segmenting different types of imaging data and/or lesions from different types of tissues.

Such segmentation software modules are referred to specifically, in this non-limiting example, as a CT Lung segmentation module 413, a CT Liver segmentation module 414, a Generic segmentation module 415, an MRI Lung segmentation module 416, a CT Lymph node segmentation module 417, and optionally additional segmentation modules characterized according to modality and/or body location and/or type scan protocol and/or other DICOM tags (not shown).

System 400 additionally features a Registration software 411 for registering two sets of data, either globally or through refined registration. System 400 additionally features a Workflow software 412.

In operation, the user is optionally provided with a source data set and a target data set by user computer 408. The source and target data sets are of at least similar tissue and/or location in the body of the subject, but are optionally obtained at different and separated points in time and may optionally have been obtained using different modalities. The source data set features a lesion, whether previously provided or user defined as described herein. The user may optionally adjust segmentation of this lesion or define a new lesion for the source set of data.

Workflow software 412 then initiates a registration of the two sets using Registration software 411 followed by refined registration using the lesion origin as input for the refined registration algorithm. Following registration, Workflow software 412 decides which segmentation module 410 to use for segmenting the lesion on target data set. This decision is based on the tissue type or location of the original lesion and/or on the target scan modality (type of image data) and may optionally involve other DICOM tags, including but not limited to scan protocol, scanner characteristics and other such tags. Once determining the segmentation software module 410 to use, the Workflow software 412 initiates the Input determination software 419 in order to calculate and determine the correct input for the segmentation software module 410. Once this input is calculated, the Workflow software 412 supplies this input to the segmentation software module 410 and initiates the segmentation. After the module segments the lesion on the target data set, Workflow software 412 calculates additional parameters for the two lesions such as growth rate, doubling time and other such information.

According to at least some embodiments of the present invention, the methods described above may optionally be applied to object features obtained from any type of imaging data, in which the object features change over time (but otherwise remain in the same general location with regard to the imaging data, such that registration is possible between different sets of imaging data taken at different time points). Non-limiting examples of suitable object features include trees or bodies of water that may grow, shrink, and change color, for which imaging data may optionally be obtained for example through satellite image data. In this case, the "subject" for example may optionally comprise a geographical area.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A method for automatically determining an input for segmentation of one or more lung lesions in a plurality of sets of image data from a subject, comprising:
providing an input set of image data that has been segmented with the lesion and a target set of image data, wherein registration cannot align the lesion in the target set of image data because the lesion has changed shape such that the registration cannot be applied to the lesion with the changed shape with a combination of only rotations, translations, scaling and shearing and in which a registration modeled by a registration matrix of the input set of image data to the target set of image data cannot align the input lesion to the target lesion, the target set of image data being obtained at a different and separated point in time from the input set of image data, the different and separated point in time being separated by at least one day;
determining a threshold that selects only low-intensity data points;
dilating initial segmentation of the input image data within the threshold to create a larger image region about the initial segmentation of the lesion in the input image data;
transforming the mask from the initial set of image data to the target set of image data according to a registration between the input and the target sets of image data to form a transformed mask;
determining a threshold mask that selects high intensity voxels;
combining the threshold mask and the transformed mask to form the combined mask; and
selecting a point within the combined mask that lies furthest from the mask boundaries to form the input for segmentation.

2. The method of claim 1, wherein the segmenting the lesion feature in target set of data is performed according to a different segmentation algorithm than a segmentation algorithm for performing the segmenting in the source set.

3. A method for automatically determining an input for one or more lesions for lesion feature segmentation in a plurality of sets of image data from the same subject, comprising:
providing an input set of image data having an initial segmentation of the lesion feature and a target set of image data, wherein registration cannot align the lesion in the target set of image data because the lesion has changed shape such that the registration cannot be applied to the lesion with the changed shape with a combination of only rotations, translations, scaling, and shearing and in which a registration modeled by a registration matrix of the input set of image data to the target set of image data cannot align the input lesion to the target lesion, the target set of image data being obtained at a different and separated point in time from the input set of image data, the different and separated point in time being separated by at least one day;
determining a guide from the initial segmentation;
transforming the guide from the initial set of image data to the target set of image data according to a registration between the initial and the target sets of image data;
analyzing the target image data according to the guide to determine a region of interest; and
automatically selecting one or more points in the target set of data according to the region of interest to form the input for segmentation of the lesion feature in the target set of data.

4. The method of claim 3, further comprising improving registration between the initial set of data and the target set of data to form improved registration after the analyzing the target image data; wherein the selecting one or more points is performed according to the improved registration.

5. The method of claim 4, wherein the improving the registration, the transforming the guide and the analyzing the target image data are performed iteratively.

6. The method of claim 3, further comprising automatically determining one or more of longest diameter or a second diameter of the lesion.

7. The method of claim 3, further comprising automatically determining changes in lesion size over time.

8. The method of claim 3, further comprising automatically determining changes in lesion density or texture, or a combination thereof.

9. The method of claim 3, further comprising determining growth rate or doubling time of the lesion, or a combination thereof.

10. The method of claim 3, wherein the source set of data comprises a different type of image data than the target set of data and wherein the above steps are performed automatically with the different type of image data.

11. The method of claim 3, wherein the segmenting the lesion feature in target set of data is performed according to a different segmentation algorithm than a segmentation algorithm for performing the segmenting in the source set.

12. The method of claim 11, wherein the segmentation algorithms are selected according to one or more of a type of image data, a tissue location of the lesion in the subject or a scan protocol.

13. The method of claim 3, wherein the performing the registration process further comprises performing a refined registration process between the source and target sets of image data optimized for a local region selected according to the provided segmentation for at least one lesion.

14. The method of claim 13, wherein the performing the refined registration process comprises performing the process locally for each lesion.

15. The method of claim 3, wherein said guide comprises one or more of a resulting point or set of points, a mask or a probability map regarding the segmentation of the lesion in the source set.

16. The method of claim 3, wherein said determining the guide further comprises analyzing the input set of image data to learn features and statistics of the lesion feature and nearby image region.

17. A method for automatically determining an input for segmentation of one or more lesions in a plurality of sets of image data from a subject, comprising:
- providing an input set of image data that has been segmented with the lesion and a target set of data, wherein registration cannot align the lesion in the target set of image data because the lesion has changed shape such that the registration cannot be applied to the lesion with the changed shape with a combination of only rotations, translations, scaling and shearing and in which a registration modeled by a registration matrix of the input set of image data to the target set of image data cannot align the input lesion to the target lesion, the target set of image data being obtained at a different and separated point in time from the input set of image data, the different and separated point in time being separated by at least one day;
- analyzing intensity statistics of the input segmented lesion and its nearby background;
- dilating initial segmentation of the input image data, forming a new mask;
- transforming the resulting mask from the initial set of image data to the target set of image data according to a registration between the initial and the target sets of image data to form a transformed mask;
- computing thresholds for the lesion in the target set of image data;
- combining the threshold mask with the transformed mask to form a combined mask;
- optionally selecting the largest connected component within the combined mask to form the resulting mask;
- dilating the resulting mask to cover the full extent of the lesion in the target set of image data;
- optionally performing morphological operations to improve the shape of the lesion after the dilation; and
- computing the line segment corresponding to the longest axial diameter of the resulting shape to form the input.

18. The method of claim 17, wherein the source set of data comprises a different type of image data than the target set of data and wherein the above steps are performed automatically with the different type of image data.

19. The method of claim 17, wherein the segmenting the lesion feature in target set of data is performed according to a different segmentation algorithm than a segmentation algorithm for performing the segmenting in the source set.

* * * * *